United States Patent
Sterling et al.

[11] Patent Number: 5,702,420
[45] Date of Patent: Dec. 30, 1997

[54] MOTORIZED SUCTION PUNCH FORCEPS

[75] Inventors: Anthony P. Sterling, Wolcott; Albert Palmero, Middlefield, both of Conn.

[73] Assignee: Anthony R. Sterling and Tri-tech, Inc., Waterbury, Conn.

[21] Appl. No.: 592,623

[22] Filed: Jan. 26, 1996

Related U.S. Application Data

[63] Continuation of Ser. No. 259,448, Jun. 14, 1994, abandoned.

[51] Int. Cl.$^6$ ............................................... A61B 17/28
[52] U.S. Cl. .................. 606/205; 606/170; 606/174; 606/83; 310/47; 30/228
[58] Field of Search ..................... 606/170, 174, 606/83, 205; 604/22; 128/751, 752, 755; 310/12, 47; 30/180, 245, 254, 228, 247, 187; 74/58, 50

[56] References Cited

U.S. PATENT DOCUMENTS

| | | |
|---|---|---|
| 4,390,827 | 6/1983 | Imahashi . |
| 5,212,887 | 5/1993 | Farmerie ........................ 30/393 |
| 5,217,460 | 6/1993 | Knoepfler ........................ 606/52 |
| 5,258,007 | 11/1993 | Spetzler et al. ................. 606/208 |
| 5,286,255 | 2/1994 | Weber ............................. 604/22 |
| 5,375,330 | 12/1994 | Herrmann ....................... 30/228 |

OTHER PUBLICATIONS

Page 35 of "1994 Products Catalog" by Linvatec, Largo, Florida.

*Primary Examiner*—Michael Buiz
*Assistant Examiner*—Daphna Shai
*Attorney, Agent, or Firm*—John H. Crozier

[57] ABSTRACT

In a preferred embodiment, a suction punch forceps, including: a body; a hollow tube attached to the body at the proximal end of the hollow tube and extending therefrom; a shaft disposed within the hollow tube for axial back-and-forth movement therein; a punch member rotatably attached to the distal end of the hollow tube and attached to the shaft such that each back-and-forth movement cycle of the shaft will cause the punch to make a cutting motion to cut tissue which is in contact with the punch member; and an electric motor attached to drive the shaft in the back-and-forth movement.

3 Claims, 4 Drawing Sheets

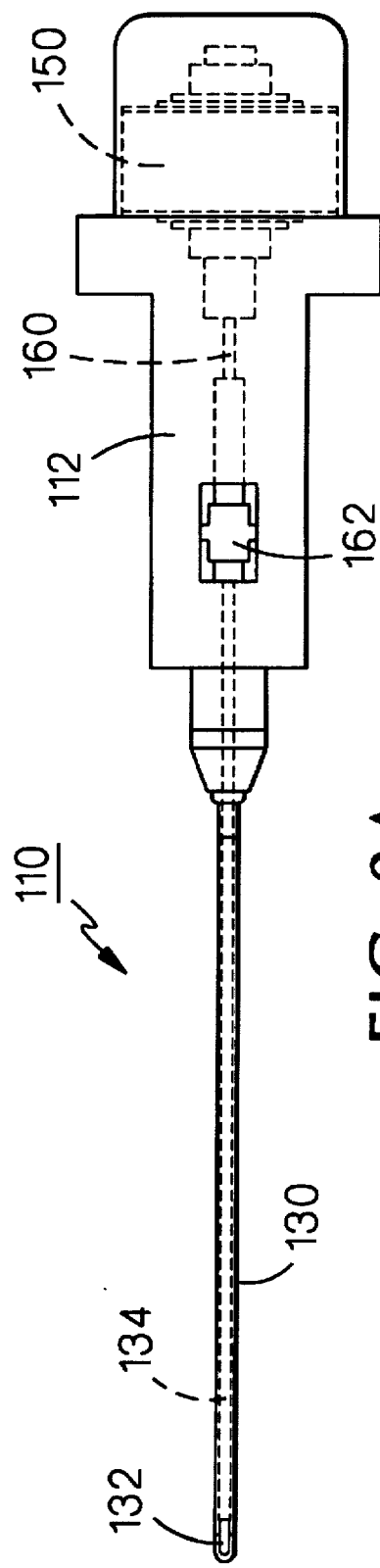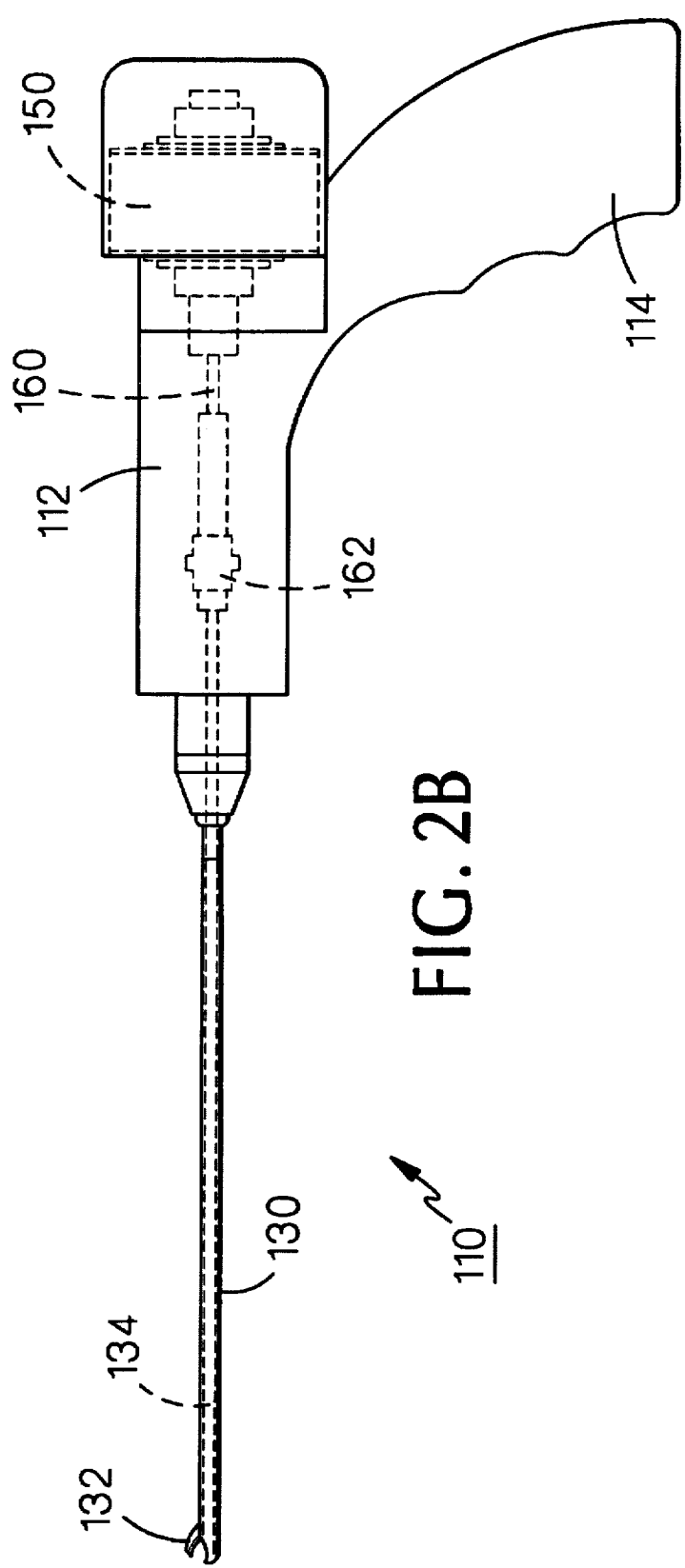
FIG. 2A
FIG. 2B

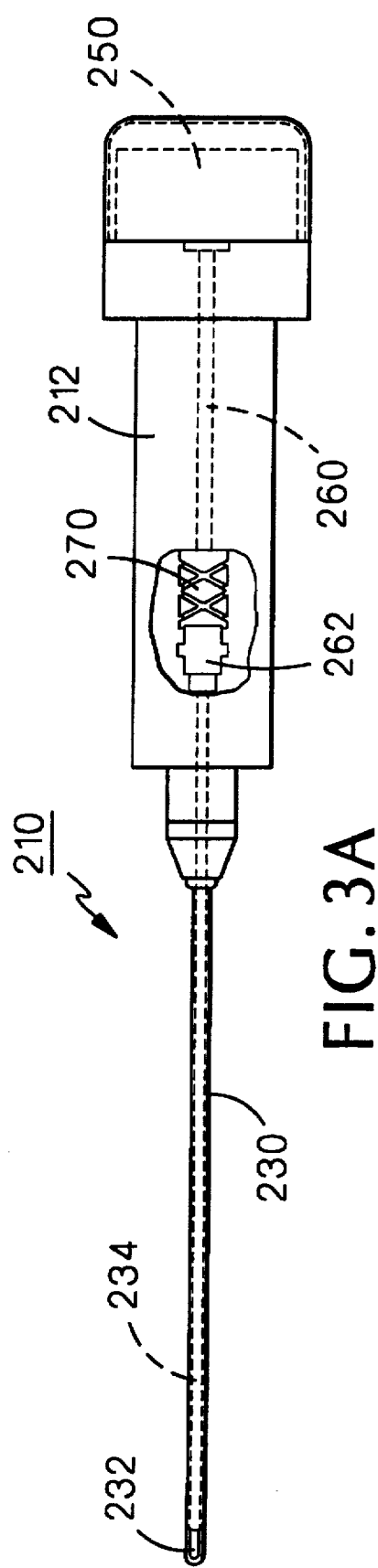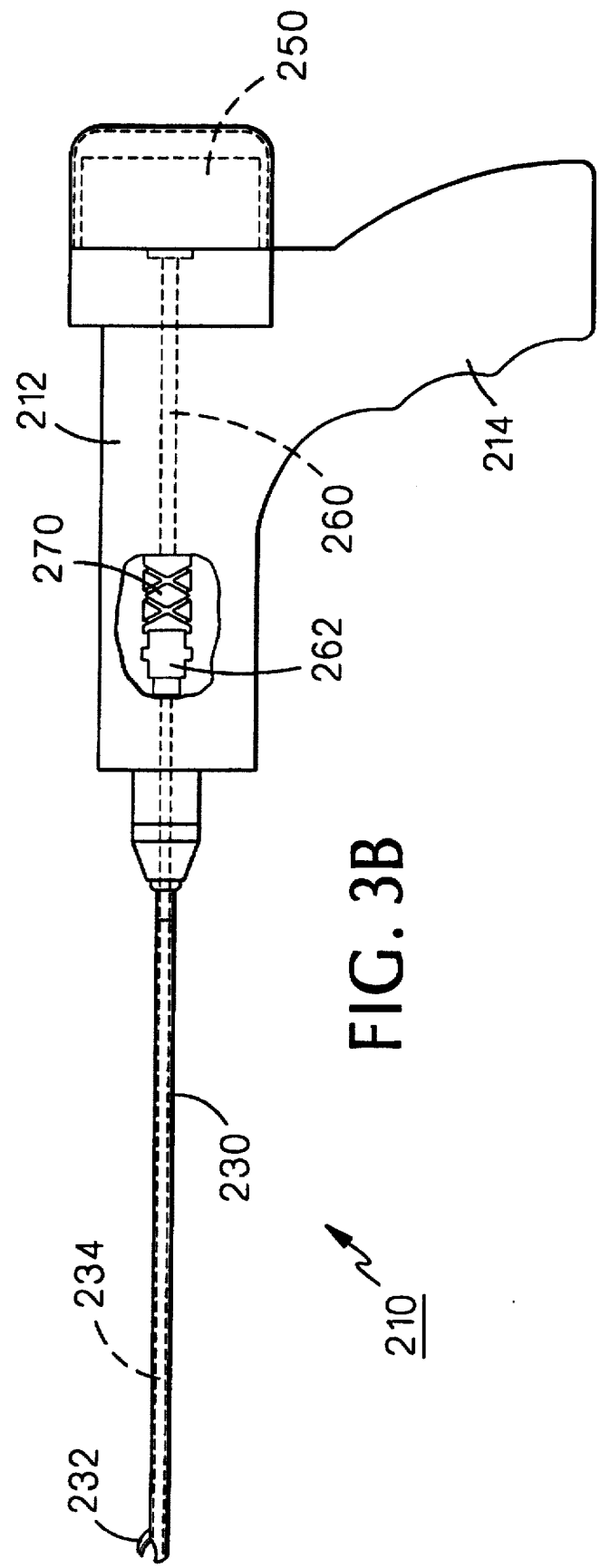
FIG. 3A
FIG. 3B

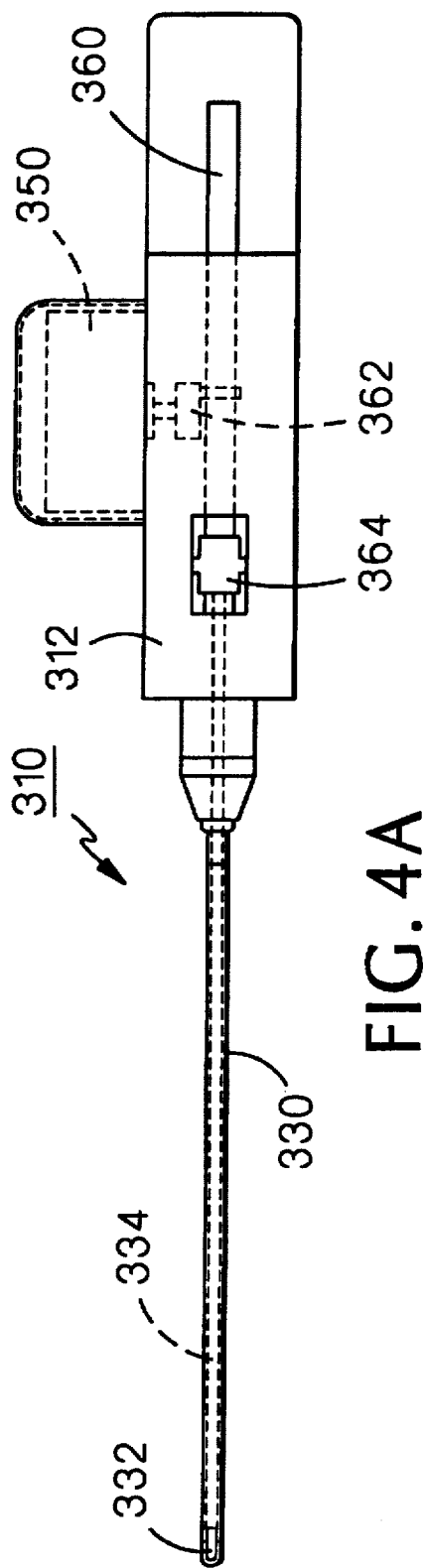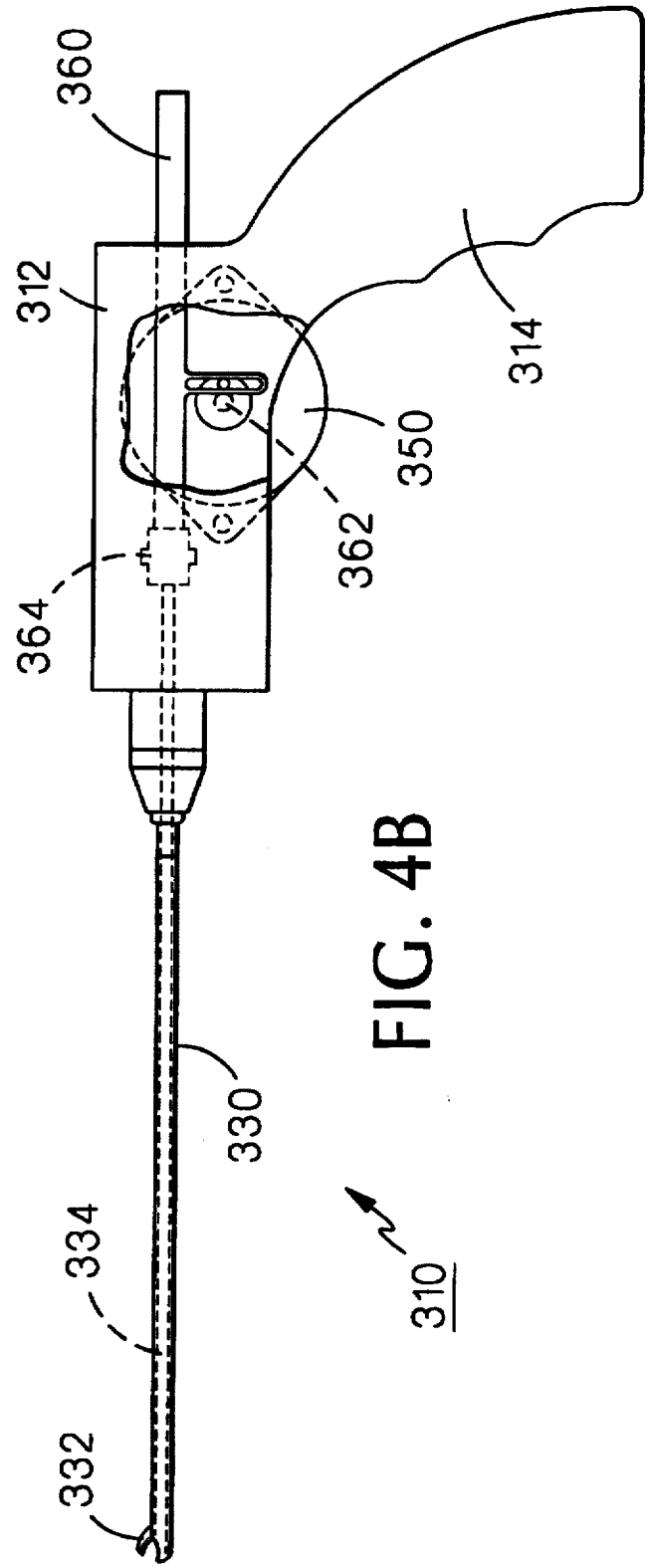

MOTORIZED SUCTION PUNCH FORCEPS

This is a continuation of application Ser. No. 08/259,448 filed on Jun. 14, 1994 now abandoned.

BACKGROUND OF THE INVENTION

1. Field of the Invention

The present invention relates to medical instruments generally and, more particularly, but not by way of limitation, to a novel motorized suction punch forceps.

2. Background Art

Suction punch forceps are universally employed in arthroscopic and endoscopic surgical procedures to excise tissue. Such forceps include a sharp cutter, or punch, at the distal end of a hollow tube. At the proximal end of the hollow tube is a body having opposed fixed and rotatable grips attached thereto. The cutting action of the punch results from manually grasping the grips and squeezing the grips so as to move the rotatable grip toward the fixed grip. Each such motion results in one "bite" of the punch. Excised tissue is aspirated from the tube by a vacuum source.

While the suction punch forceps operates satisfactorily as described above, a surgeon may employ the forceps for as many as five or six procedures a day. The pressure required to operate the forceps is only a few ounces; however, repeated, rapid squeezing of the grips can result in uni- and bi-lateral carpal tunnel syndromes and epicondylitis or tendonitis of the forearm and hand.

Accordingly, it is a principal object of the present invention to provide a suction punch forceps that requires no manually squeezing of the grips.

It is a further object of the invention to provide such a suction punch forceps that is easily used and controlled.

It is an additional object of the invention to provide such a suction punch forceps that is economically constructed.

Other objects of the present invention, as well as particular features, elements, and advantages thereof, will be elucidated in, or be apparent from, the following description and the accompanying drawing figures.

SUMMARY OF THE INVENTION

The present invention achieves the above objects, among others, by providing, in a preferred embodiment, a suction punch forceps, comprising: a body; a hollow tube attached to said body at the proximal end of said hollow tube and extending therefrom; a shaft disposed within said hollow tube for axial back-and-forth movement therein; a punch member rotatably attached to the distal end of said hollow tube and attached to said shaft such that each back-and-forth movement cycle of said shaft will cause said punch to make a cutting motion to cut tissue which is in contact with said punch member; and an electric motor attached to drive said shaft in said back-and-forth movement.

BRIEF DESCRIPTION OF THE DRAWING

Understanding of the present invention and the various aspects thereof will be facilitated by reference to the accompanying drawing figures, submitted for purposes of illustration only and not intended to define the scope of the invention, which is a side elevational view of a suction punch forceps constructed according to the present invention, on which:

FIGS. 2A and 2B are top plan and side elevational views, respectively, of another embodiment of the present invention.

FIGS. 3A and 3B are top plan and side elevational views, respectively, partially cut-away, of a further embodiment of the present invention.

FIGS. 4A and 4B are top plan and side elevational views, respectively, of an additional embodiment of the present invention.

DETAILED DESCRIPTION OF THE PREFERRED EMBODIMENTS

Figure 1:
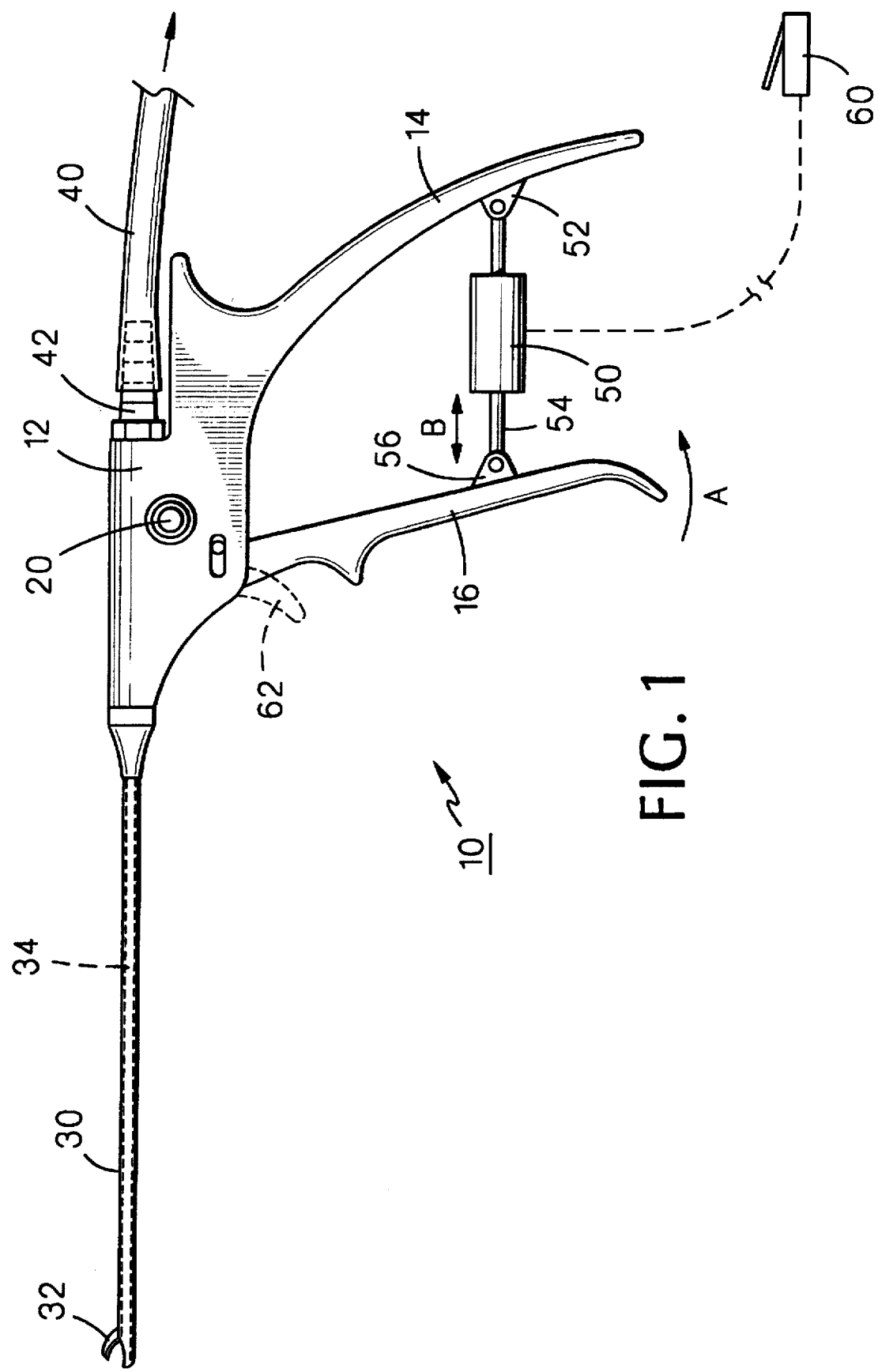
FIG. 1 is a side elevational view of one embodiment of the present invention.

FIG. 1 illustrates a suction punch forceps constructed according to the present invention, generally indicated by the reference numeral 10. Forceps 10 includes a body portion 12 having an integral grip 14 depending therefrom. A moveable grip 16 depends from body portion 12 opposed and generally horizontal to fixed grip 14 and is rotatably attached to body portion 12 by a shaft 20 so that the distal end of the moveable grip can be manually advanced toward fixed grip 14 in the direction indicated by arrow "A".

A hollow tube 30 extends forwardly from body portion 12 and has a punch member 32 rotatably mounted at the distal end thereof. A shaft 34 axially moveable within hollow tube 30 is operatively connected between punch member 32 and the proximal end of moveable grip 16 such that each movement of the moveable grip toward fixed grip 14 causes the punch to take a "bite" of tissue (not shown). Particles of tissue can be removed from forceps 10 through tube 30 by means of an external tube 40 having one end attached to a fitting 42 on body portion 12 and the other end attached to a source of vacuum (not shown).

As described so far, suction punch forceps 10 is conventional and may be a Shutt Suction Punch Forceps as furnished by Linvatec, of Largo, Fla.

The present invention overcomes the disadvantages of conventional suction punch forceps by providing, in the embodiment of the present invention illustrated on FIG. 1, a linear motor 50 disposed between fixed grip 14 and moveable grip 16. Motor 50 is rotatably attached to a flange 52 fixedly attached to fixed grip 14 and has its shaft 54 rotatably attached to a flange 56 fixedly attached to moveably grip 16. Shaft 54 is moveable as indicated by arrow "B" to alternatingly move moveable grip 16 toward and away from fixed grip 14, thus causing repeated punching action of punch 32.

Suction punch forceps 10 is preferably operated by a foot switch 60 which provides off and on control, as well as selective control of rate of punching of the forceps. Alternatively, a trigger switch 62 can be provided on forceps 10 to provide the same modes of control. A rate of between 20 and 200 punches per minute is preferred.

Punching action of forceps 10 is fully automated and completely eliminates the problems present with conventional suction punch forceps.

Suction punch forceps 10 is economically constructed, is easily used, and can be sterilized with conventional sterilization equipment.

FIGS. 2A and 2B illustrate a suction punch forceps constructed according to another embodiment of the present invention, generally indicated by the reference numeral 110. Elements of forceps 110 similar to those of forceps 10 on FIG. 1 are given the same reference numerals, with the addition of the prefix "1".

Forceps 110 is operated by a linear motor 150 mounted at the rear of body portion 112. Linear motor 150 has a motor shaft 160 extending therefrom attached by a coupling 162 to shaft 134 to operate forceps 110 in the manner described above with reference to forceps 10. Control of forceps 110 may be with a trigger or a foot switch, such as trigger 62 or foot switch 60 shown on FIG. 1. Suitable provision can be made for aspirating pieces of tissue from forceps 110.

FIGS. 3A and 3B illustrate a suction punch forceps constructed according to a further embodiment of the present invention, generally indicated by the reference numeral 210. Elements of forceps 210 similar to those of forceps 10 on FIG. 1 are given the same reference numerals, with the addition of the prefix "2".

Forceps 210 is operated by a rotary motor 250 mounted at the rear of body portion 112. Rotary motor 250 has a motor shaft 260 extending therefrom attached by a coupling 262 to shaft 234 to operate forceps 210 in the manner described above with reference to forceps 10. Axial movement of shaft 234 is provided by means of a self-reversing double-helix mechanism 270. Control of forceps 210 may be with a trigger or a foot switch, such as trigger 62 or foot switch 60 shown on FIG. 1. Suitable provision can be made for aspirating pieces of tissue from forceps 210.

FIGS. 4A and 4B illustrate a suction punch forceps constructed according to another embodiment of the present invention, generally indicated by the reference numeral 310. Elements of forceps 310 similar to those of forceps 10 on FIG. 1 are given the same reference numerals, with the addition of the prefix "3".

Forceps 310 is operated by a rotary motor 350 mounted at the rear of body portion 312. Rotary motor 350 drives an axially moving shaft 360 through a rotary-to-linear motion converter, in this case, a bell crank 362. Shaft 360 is connected to shaft 334 through a coupling 364 to operate forceps 310 in the manner described above with reference to forceps 10. Control of forceps 310 may be with a trigger or a foot switch, such as trigger 62 or foot switch 60 shown on FIG. 1. Suitable provision can be made for aspirating pieces of tissue from forceps 310.

It will thus be seen that the objects set forth above, among those elucidated in, or made apparent from, the preceding description, are efficiently attained and, since certain changes may be made in the above construction without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

We claim:

1. A suction punch forceps, comprising:

(a) a body;

(b) a hollow tube attached to said body at a proximal end of said hollow tube and extending from said body;

(c) a drive shaft disposed within said hollow tube for axial back-and-forth movement therein;

(d) an electric motor attached to said drive shaft to drive said drive shaft in back-and-forth movement;

(e) means for rotatably attaching a punch member to said distal end of said hollow tube and attached to said drive shaft such that each back-and-forth movement cycle of said shaft will cause said punch member to make a cutting motion to cut tissue which is in contact with said punch member;

(f) a first handle fixedly attached to said body and extending therefrom;

(g) a second handle rotatably attached to said body and extending therefrom, a distal end of said second handle being rotatable toward and away from said first handle and means for operatively attaching said second handle to said drive shaft to cause said back-and-forth movement thereof when said second handle is rotated toward and away from said first handle; and (h) said electric motor is attached between said first and second handles to cause said rotation of said second handle toward and away from said first handle.

2. A suction punch forceps, as defined in claim 1, further comprising: control means to control the rate of said back-and-forth movement.

3. A suction punch forceps, as defined in claim 1, wherein: said electric motor is a linear motor.

* * * * *